United States Patent
Kurata et al.

(10) Patent No.: US 8,207,367 B2
(45) Date of Patent: Jun. 26, 2012

(54) METHOD FOR PRODUCING POLYMERIZABLE PHOSPHATE ESTER

(75) Inventors: Minoru Kurata, Wakayama (JP); Keishi Shimokawa, Wakayama (JP)

(73) Assignee: Kao Corporation, Tokyo (JP)

( * ) Notice: Subject to any disclaimer, the term of this patent is extended or adjusted under 35 U.S.C. 154(b) by 465 days.

(21) Appl. No.: 12/159,332

(22) PCT Filed: Dec. 26, 2006

(86) PCT No.: PCT/JP2006/326339
§ 371 (c)(1),
(2), (4) Date: Oct. 3, 2008

(87) PCT Pub. No.: WO2007/074926
PCT Pub. Date: Jul. 5, 2007

(65) Prior Publication Data
US 2010/0227994 A1   Sep. 9, 2010

(30) Foreign Application Priority Data

Dec. 26, 2005  (JP) ................... 2005-371244
Jul. 6, 2006  (JP) ................... 2006-186352

(51) Int. Cl.
*C07F 9/113*   (2006.01)

(52) U.S. Cl. ........ 558/114; 526/277; 526/321; 528/398; 558/113; 558/118; 558/119; 558/152; 558/156; 558/161; 558/163; 558/177; 558/207; 558/208; 558/218; 562/8; 562/20; 562/23; 562/878; 568/8

(58) Field of Classification Search ........... 526/277, 526/321; 558/113, 114, 118, 119, 152, 156, 558/161, 163, 177, 207, 208, 218; 562/8, 562/20, 23, 878; 568/8; 528/398
See application file for complete search history.

(56) References Cited

FOREIGN PATENT DOCUMENTS

| | | |
|---|---|---|
| JP | 5 306208 | 11/1993 |
| JP | 2000 327386 | 11/2000 |
| JP | 2003 146992 | 5/2003 |
| WO | 02 088151 | 11/2002 |
| WO | WO 02-088151 | * 11/2002 |

OTHER PUBLICATIONS

Pesticide Formulations and Application Systems, vol. 15, eds. Herbert M. Collins, Franklin R. Hall, Michael Hopkinson, ASTM International, 1996, pp. 99-101.*
Kobunshi Kako (Polymer Application), 1990, 39(2), 38-39.*
Translation of Kobunshi Kako (Polymer Application), 1990, 39(2), 38-39.*
Translation of WO 2002/088151.*
Extended European Search Report issued Apr. 1, 2011, in European Patent Application No. 06843712.8.
Office Action issued Nov. 2, 2011, in European Patent Application No. 06 843 712.8.

* cited by examiner

*Primary Examiner* — Vasu Jagannathan
*Assistant Examiner* — Richard A Huhn
(74) *Attorney, Agent, or Firm* — Oblon, Spivak, McClelland, Maier & Neustadt, L.L.P.

(57) ABSTRACT

The present invention relates to a method of producing a polymerizable phosphate containing at least one selected from polymerizable phosphates represented by formula (II), (III) or (IV) by a batch reaction, including a step of adding a compound represented by formula (I) into a mixture of a polymerizable phosphate reaction product containing at least one selected from polymerizable phosphates represented by formula (II), (III) or (IV), obtained by a pre-batch reaction, and phosphoric acid anhydride to react them:

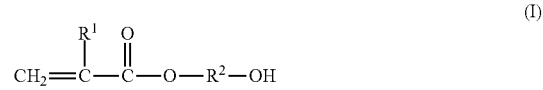

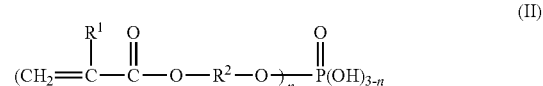

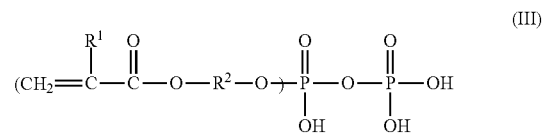

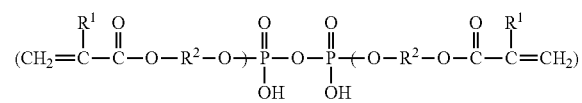

wherein $R^1$ represents H or a $C_{1-4}$ alkyl group, $R^2$ represents a $C_{2-6}$ alkylene group and n denotes an integer from 1 to 3.

16 Claims, 1 Drawing Sheet

METHOD FOR PRODUCING POLYMERIZABLE PHOSPHATE ESTER

FIELD OF THE INVENTION

The present invention relates to a method of producing a polymerizable phosphate.

BACKGROUND OF THE INVENTION

Polymerizable phosphates are obtained, for example, by reacting an unsaturated group-containing alcohol with phosphoric acid anhydride or polyphosphoric acid. JP-A 2003-146992 discloses a method in which a phosphoric acid anhydride suspension solution is added dropwise to an unsaturated group-containing alcohol in the presence of a reducing agent, followed by continuous stirring to thereby produce a polymerizable phosphate improved in hue. Also, WO-A 2002/088151 discloses a method of producing a polymerizable phosphate reduced in the contents of a volatile solvent and polymerizable organic acids produced as byproducts by allowing a polyphosphoric acid and at least one of hydroxyalkyl-α-substituted acrylate to undergo an esterification reaction using a polymerizable phosphate as a reaction solvent.

SUMMARY OF THE INVENTION

The present invention relates to a method of producing a polymerizable phosphate containing at least one selected from polymerizable phosphates represented by formula (II), (III) or (IV) by a batch reaction, including a step of adding a compound represented by formula (I) into a mixture of a polymerizable phosphate reaction product containing at least one selected from polymerizable phosphates represented by formula (II), (III) or (IV), obtained by a pre-batch reaction, and phosphoric acid anhydride to react them:

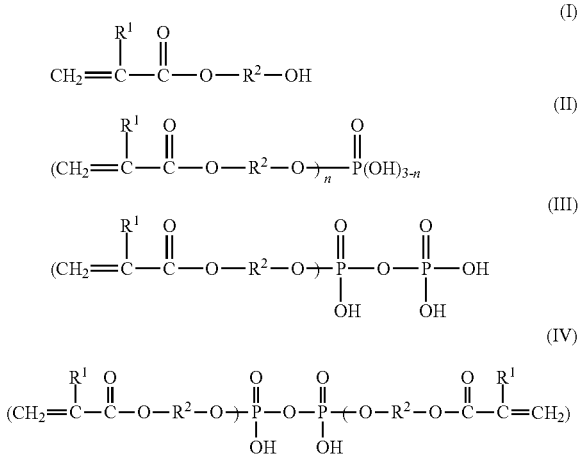

$$CH_2=\overset{R^1}{\underset{}{C}}-\overset{O}{\underset{}{C}}-O-R^2-OH \quad (I)$$

$$(CH_2=\overset{R^1}{\underset{}{C}}-\overset{O}{\underset{}{C}}-O-R^2-O)_n-\overset{O}{\underset{}{P}}(OH)_{3-n} \quad (II)$$

$$(CH_2=\overset{R^1}{\underset{}{C}}-\overset{O}{\underset{}{C}}-O-R^2-O)_n-\overset{O}{\underset{OH}{P}}-O-\overset{O}{\underset{OH}{P}}-OH \quad (III)$$

$$(CH_2=\overset{R^1}{\underset{}{C}}-\overset{O}{\underset{}{C}}-O-R^2-O)_n-\overset{O}{\underset{OH}{P}}-O-\overset{O}{\underset{OH}{P}}(-O-R^2-O-\overset{O}{\underset{}{C}}-\overset{R^1}{\underset{}{C}}=CH_2) \quad (IV)$$

wherein $R^1$ represents a hydrogen atom or a straight-chain or branched alkyl group having 1 to 4 carbon atoms, $R^2$ represents a straight-chain or branched alkylene group having 2 to 6 carbon atoms and n denotes an integer from 1 to 3.

The present invention also relates to a hydraulic composition dispersant obtained by copolymerizing the above produced polymerizable phosphate with a monomer represented by formula (V).

DETAILED DESCRIPTION OF THE INVENTION

The compounds synthesized in JP-A 2003-146992 and WO-A 2002/088151 are accompanied by byproducts obtained in various side reactions. Therefore, these compounds contain a large amount of impurities and particularly, compounds having no polymerizable double bond and compounds which contain no phosphoric acid group though they have polymerizable double bonds.

Therefore, there is the problem that no intended performance is obtained when the polymerizable phosphate obtained by the above current methods is polymerized as it is or copolymerized with a copolymerizable compound to obtain an intended product. Also, the polymerizable phosphate obtained in the above current method may be highly purified according to the need to thereby raise the content of effective components. However, this method has the problem that the reduction in the content of effective components in synthesis brings about an increase in refining load and a reduction in yield.

Therefore, it has been desired to establish a method of synthesizing a polymerizable phosphate having a high effective content. However, no teaching concerning this method has been disclosed so far.

The present invention relates to a method of producing a polymerizable phosphate having a high effective content while limiting side-reactions.

According to the present invention, a phosphate having a high effective content can be obtained. A polymer of the product obtained by the present invention is utilized as a cement dispersant.

The effective components of the polymerizable phosphate in the present invention are a monoester represented by formula (II) in which n=1, a diester represented by formula (II) in which n=2, a triester represented by formula (II) in which n=3, a pyromonoester represented by formula (III) and a pyrodiester represented by formula (IV). The polymerizable phosphate reaction product contains the above effective components and components other than the above effective components. Also, the effective content of the polymerizable phosphate is the weight percentage of the total weight of the effective components of the above polymerizable phosphate based on the total weight of the reaction products.

In the present invention, phosphoric acid anhydride is used as the phosphorylating agent, and in this case, a part or preferably 20% by weight or less of the phosphoric acid anhydride may be substituted with 60 to 100% by weight and preferably 75% by weight of phosphoric acid.

In the compounds represented by formulae (I) to (IV) and used in the present invention, $R^1$ represents a hydrogen atom or an alkyl group having 1 to 4 carbon atoms and is preferably a methyl group. $R^2$ represents a straight-chain or branched alkylene group having 2 to 6 carbon atoms and is preferably an ethylene group. n denoted an integer from 1 to 3 and is preferably 1 or 2.

In the present invention, the polymerizable phosphate reaction product obtained in the pre-batch operation is first mixed with phosphoric acid anhydride. A polymerizable phosphate having a higher effective content than in the case of reacting phosphoric acid anhydride with the compound (I) by reacting the compound (I) after polymerizable phosphate reaction product obtained in the pre-batch operation is mixed with phosphoric acid anhydride.

When the weight of the polymerizable phosphate reaction product obtained in the pre-batch operation for mixing is A and the total weight of the phosphorylating agent and compound (I) used in an addition reaction is B in the present invention, the total amount T charged to the reaction vessel is the sum of A and B. The amount A is preferably 30% by weight or more, more preferably 50% by weight or more and even more preferably 60% by weight or more from the viewpoint of decreasing the viscosity obtained after it is mixed with phosphoric acid anhydride and increasing the effective content of the polymerizable phosphate. Also, the amount A is preferably 90% by weight or less and more preferably 80% by weight or less from the viewpoint of the productivity of the polymerizable phosphate per volume of the reaction vessel.

The polymerizable phosphate reaction product obtained in the pre-batch operation for mixing is preferably a polymerizable phosphate having a high effective content though there is no particular limitation to the reaction product. As the polymerizable phosphate reaction product, a polymerizable phosphate having an effective content of 40% by weight or more is used.

The content of the phosphorylating agent in the polymerizable phosphate reaction product and phosphoric acid anhydride to be mixed is preferably 2 to 30% by weight and more preferably 5 to 20% by weight based on the total weight of the mixture from the viewpoint of increasing the effective content and limiting an increase in the viscosity of the system.

In the present invention, the ratio of phosphoric acid anhydride to the compound (I) to be charged may be optionally designed according to the composition of a desired polymerizable phosphate. In the case, for example, a monoester is obtained as a major component, it is preferable to use phosphoric acid anhydride in an amount of 0.4 to 0.6 times as many mole as the compound (I), more preferably 0.5 times, and water in an amount of 0.4 to 0.6 times as many mole as the compound (I), more preferably 0.5 times. When a large amount of a diester is obtained, it is preferable to use phosphoric acid anhydride in an amount of 0.25 to 0.4 times as many mole as the compound (I), more preferably 1/3 times. If the ratio of phosphoric acid to water to be charged is set to a desired one, the ratio of a monoester to a diester can be controlled. However, when a polyphosphoric acid is used in place of the above phosphorous acid anhydride, the freeness of the composition of the obtained phosphate is decreased.

The above phosphoric acid anhydride may be charged by supplying a powder directly or by suspending it in an organic solvent inert thereto. When phosphorous acid anhydride is charged by suspending it in an organic solvent, it is necessary to remove the organic solvent after the reaction is finished and it is therefore preferable to charge the powder directly.

In the method of the present invention, it is preferable to use a polymerization inhibitor to suppress polymerization in the phosphorylating reaction. Examples of the polymerization inhibitor include hydroquinones such as hydroquinone, methoxyhydroquinone and di-t-butylhydroquinone; naphthols such as α-naphthol and β-naphthol; catechols such as catechol and di-t-butylcatechol; parabenzoquinone; pyrogallols such as pyrogallol and phenylethyl pyrogallol; anisoles such as 2,6-di-t-butylanisol; thiodiphenylamine and sulfur-type polymerization inhibitors such as a sulfur powder.

The polymerization inhibitor is used in an amount of preferably 10 ppm to 1.0% by weight and more preferably 10 to 2000 ppm based on the total weight of the compound (I) and phosphoric acid anhydride.

In the present invention, the temperature at which the compound (I) is added to phosphorylate is preferably 100° C. or less, more preferably 90° C. or less and even more preferably 85° C. or less from the viewpoint of suppressing the production of impurities caused by side-reactions. Also, the temperature is preferably 30° C. or more, more preferably 40° C. or more and even more preferably 55° C. or more from the viewpoint of improving the heat-removal ability by cooling to thereby shorten the required time.

In the present invention, it is desirable to blow oxygen in the reaction solution from the viewpoint of preventing the polymerization reaction. The amount of oxygen to be blown is preferably 0.05 Nm$^3$/hr/m$^3$-reaction vessel or more, based on the capacity of the reaction vessel. The oxygen-blowing method may be air-blowing. Also, from the viewpoint of preventing the explosion of the component (I), the concentration of oxygen in the vapor phase in the vessel is preferably 10% or less. It is preferable to blow inert gas into the reaction vessel. The amount of the inert gas to be blown is preferably 2.1 to 3.0 times as many moles as that of oxygen to be blown. The inert gas may, for example, be nitrogen gas.

The time taken to add the compound (I) is preferably about 0.5 to 10 hours though no particular limitation is imposed to the time.

An aging reaction may be carried out in succession to the addition of the compound (I). The aging time is preferably 0.5 to 10 hours and the aging temperature is preferably 30 to 100° C.

The batch reaction in the present invention is desirably repeated from the viewpoint of raising the effective content of the polymerizable phosphate.

Also, the polymerizable phosphate obtained in the present invention may be copolymerized with a monomer represented by the following formula (V) to obtain a copolymer suitable as a hydraulic composition dispersant.

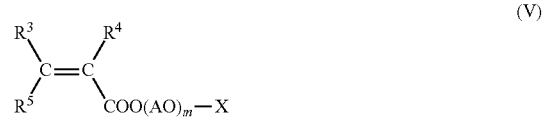

(V)

Wherein, $R^3$ and $R^4$ respectively represent a hydrogen atom or a methyl group, $R^5$ represents a hydrogen atom or —COO(AO)$_m$X, AO represents an oxyalkylene group having 2 to 4 carbon atoms or an oxystyrene group, m denotes the total addition molar number of AOs and is a number of 3 to 200 and X represents a hydrogen atom or an alkyl group having 1 to 18 carbon atoms.

With regard to the monomer (V), $R^5$ in formula (V) is preferably a hydrogen atom and AO is preferably an oxyalkylene group having 2 to 4 carbon atoms and preferably contains an ethyleneoxy group (hereinafter, EO group), wherein the ED group is preferably 70 mol % or more, more preferably 80 mol % or more, even more preferably 90 mol % or more, and it is even more preferable that all AO is an EO group. Also, X is a hydrogen atom or an alkyl group having preferably 1 to 18, more preferably 1 to 12, even more preferably 1 to 4, even more preferably 1 to 2 carbon atoms and even more preferably a methyl group. Specific examples of the monomer (V) include ω-methoxypolyoxyalkylenemethacrylate, ω-methoxypolyoxyalkyleneacrylate and the like and ω-methoxypolyoxyalkylenemethacrylate is more preferable. Here, m of formula (V) is 3 to 200 and preferably 4 to 120 in the point of the dispersibility of the polymer in the hydraulic composition and the effect of imparting viscosity.

In the repeated units by m on the average, AO may be different from one another and (AO)m may be random addition, block addition or a mixture of them. AO may contain a propyleneoxy group or the like besides the EO group.

In the copolymerization of the monomer, the molar ratio of the monomer (V) to the polymerizable phosphate, namely (monomer (V)/polymerizable phosphate) is preferably 5/95 to 95/5 and more preferably 10/90 to 90/10. In this case, with regard to the polymerizable phosphate, it is so designed that the mol ratio and mol % are calculated based on an acid type compound. (hereinafter the same)

The polymerizable phosphate obtained in this method contains a diester in a high ratio and is therefore expected to be significantly gelled. Therefore, this polymerizable phosphate is not usually used as the raw material for the production of polymers for hydraulic composition dispersant. However, when the monomer solution having a pH of 7 or less is used in the reaction, the gelation is suppressed and a phosphate polymer suitable as a hydraulic composition dispersant can be manufactured at an industrially practical level.

More preferable production conditions are described below from the viewpoint of suppressed gelation, controlling an appropriate molecular weight and designing the performance of the hydraulic composition dispersant. From this point of view, a chain transfer agent is preferably used in an amount of preferably 4 mol % or more, more preferably 6 mol or more and even more preferably 8 mol % or more based on the total mols of the polymerizable phosphate and monomer (V). The upper limit of the amount of the chain transfer agent to be used is preferably 100 mol or less, more preferably 60 mol % or less, even more preferably 30 mol % or less and even more preferably 15 mol % or less. To state in more detail:

(1) In the case where m in the monomer (V) is 3 to 30;

(1-1) when the molar ratio of the polymerizable phosphate in the polymerizable phosphate and monomer (V) exceeds 50 mol %, the chain transfer agent is used in an amount of preferably 6 to 100 mol % and more preferably 8 to 60 mol % based on the polymerizable phosphate and monomer (V);

(1-2) when the molar ratio of the polymerizable phosphate in the polymerizable phosphate and monomer (V) is less than 50 mol %, the chain transfer agent is used in an amount of preferably 4 to 60 mol % and more preferably 5 to 30 mol % based on the polymerizable phosphate and monomer (V); and (2) In the case where m in the monomer (V) exceeds 30; the chain transfer agent is used in an amount of preferably 6 to 50 mol % and more preferably 8 to 40 mol % based on the polymerizable phosphate and monomer (V) in the polymerizable phosphate.

In the production method in the present invention, it is preferable to run the reaction of the polymerizable phosphate at a target reaction rate of preferably 60% or more, more preferably 70% or more, even more preferably 80% or more, even more preferably 90% or more and even more preferably 95% or more. The amount of the chain transfer agent may be selected from this point of view. Here, the reaction rate of the polymerizable phosphate may be calculated by the following equation.

$$\text{Reaction rate}(\%) = (1 - Q/P) \times 100$$

where;

Q: ratio of the polymerizable phosphates represented by formulae (II), (III) and (IV) for X derived from the monomer (V) in the reaction system after the reaction is finished; and P: ratio of the polymerizable phosphates represented by formulae (II), (III) and (IV) for X derived from the monomer (V) in the reaction system after the reaction is started.

The ratio (mol %) of the polymerizable phosphate in a phosphorous-containing compound in a reaction system when the reaction is started or finished may be calculated based on the above results of $^1$H-NMR.

In the production of the phosphate polymer according to the present invention, polymerizable monomers other than the above polymerizable phosphate and the monomer (V) may be used. Examples of these other polymerizable monomer may include allylsulfonic acid and methallylsulfonic acid, alkali metal salts, alkali earth metal salts, ammonium salts and amine salts of any of these acids. Also, examples of these other polymerizable monomer may include acrylic acid type monomers such as acrylic acid, methacrylic acid, crotonic acid, maleic acid, fumaric acid, itaconic acid and citraconic acid and also, one or more alkali metal salts, alkali earth metal salts, ammonium salts, amine salts, methyl esters and ethyl esters of these acids and anhydrous compounds such as maleic acid anhydride. Moreover, examples of these other polymerizable monomer may include (meth)acrylamide, N-methyl(meth)acrylamide, N,N-dimethyl(meth)acrylamide, 2-(meth)acrylamide-2-methasulfonic acid, 2-(meth)acrylamide-2-ethanesulfonic acid, 2-(meth)acrylamide-2-propanesulfonic acid, styrene and styrenesulfonic acid. The ratio of the total amount of the polymerizable phosphate and monomer (V) in all monomers is preferably 30 to 100 mol %, more preferably 50 to 100 mol % and even more preferably 75 to 100 mol %. The ratio of the total amount of the polymerizable phosphate and monomer (V) in all monomers is preferably an amount exceeding 95 mol % to 100 mol %, more preferably 97 to 100 mol % and even more preferably 100 mol %.

In the production method of the present invention, the reaction temperature of the polymerizable phosphate and monomer (V) is preferably 40 to 100° C. and more preferably 60 to 90° C., and the reaction pressure (gauge pressure) is preferably 101.3 to 111.5 kPa (1 to 1.1 atm) and more preferably 101.3 to 106.4 kPa (1 to 1.05 atm).

In the production method of the present invention, a monomer solution containing the above polymerizable phosphate prepared using a proper solvent is copolymerized, preferably, in the presence of a fixed amount of a chain transfer agent. Other copolymerizable monomers and a polymerization initiator may be used.

In the present invention, the polymerizable phosphate to be polymerized and the monomer (V) are preferably reacted at a pH of 7 or less. In the present invention, the pH (at 20° C.) of the reaction solution collected during the course of the reaction (start to end of the reaction) is defined as the pH in the reaction. Usually, it is only required to initiate the reaction in such a condition (ratio of the monomer, a solvent and other components) that the system in the reaction is clearly adjusted to pH 7 or less.

Here, when the reaction system is a nonaqueous system, water sufficient to measure the pH of the system may be added to the reaction system to measure.

In the case of using the polymerizable phosphate and monomer (V) which are the subjects of the present invention, the pH of the system in the reaction is also usually 7 or less in consideration of other conditions if the reaction is run in the condition exemplified in the following (1) and (2). Also, the case where the pH of the system temporally exceeds 7 is allowed to the extent that the whole reaction is not adversely affected, so that, for example, no gel is produced in the system.

(1) A monomer solution containing the polymerizable phosphate and the monomer (V) and having a pH of 7 or less is used for the copolymerization reaction of the polymerizable phosphate and the monomer (V).

(2) The copolymerization reaction of the polymerizable phosphate and the monomer (V) is made to start at a pH of 7 or less. Specifically, a reaction system containing the polymerizable phosphate and the monomer (V) is adjusted to pH 7 or less and then is allowed to start the reaction.

To state specifically:

(i) the monomer solution containing the polymerizable phosphate and the monomer (V) is adjusted to pH 7 or less to start the copolymerization reaction;

(ii) a monomer solution (pH is optional and preferably 7 or less) containing the polymerizable phosphate and the monomer (V) is added dropwise to the reaction system;

(iii) a monomer solution (pH is optional and preferably 7 or less) containing the monomer (V) and the polymerizable phosphate (pH is optional and preferably 7 or less) are added separately to the reaction system; and (iv) the above methods are appropriately combined to run the reaction. For example, a part of the monomer solution (pH is optional and preferably 7 or less) containing the polymerizable phosphate and the monomer (V) is charged into the reaction system and the remainder monomer solution is added dropwise to the reaction system.

In the above (iii) and (iv), it is necessary to control the addition condition of the monomer solution to be added dropwise to the system such that the amount of the monomer is controlled without departing from the predetermined molar ratio of the monomer. Also, in the above (ii) to (iv), other reaction conditions are considered such that the reaction system containing the added polymerizable phosphate and the monomer (V) is adjusted to pH 7 or less and preferably 4 or less.

The pH of the reaction system may be adjusted using an inorganic acid (phosphoric acid, hydrochloric acid, nitric acid or sulfuric acid), NaOH, KOH, triethanolamine or the like according to the need.

In the present invention, as mentioned above, the pH of the monomer solution containing the polymerizable phosphate among the monomer solutions used for the reaction is preferably 7 or less to adjust the reaction system in the reaction to pH 7 or less. The monomer solution having a pH of 7 or less contains the polymerizable phosphate obtained in the present invention, and may be one containing the monomer (V) or one further containing a chain transfer agent and other monomers. Here, the monomer solution containing the polymerizable phosphate is preferably a hydrated type (specifically, the solvent contains water) in consideration of pH measurement. However, in the case of a nonaqueous type, water may be added in a necessary amount to make measurement. The pH of the system is 7 or less, preferably 0.1 to 6 and more preferably 0.2 to 4.5 from the viewpoint of the uniformity of the monomer solution, prevention of gelation and limitation to a reduction in performance. Also, the monomer (V) is preferably used in the state of a monomer solution having a pH of 7 or less. This pH is one measured at 20° C.

The pH of the reaction system (polymerization system) which is finally charged with the monomer is preferably 6 or less, more preferably 5 or less, even more preferably 4 or less and even more preferably 2 or less at 20° C. from the viewpoint of stability when the molecular weight of the polymer is controlled and easiness of pH control in the reaction. It is preferable that the pH of the monomer solution containing the polymerizable phosphate (pH of the reaction system at the initiation of the reaction), the pH of the reaction system in the course of the reaction and the pH of the reaction system when the reaction has finished are all 7 or less.

When these polymerizable phosphate and monomer (V) are not used in a hydrate state (namely, they are added dropwise as a liquid component), the pH of the polymerization system is inevitably 7 or less. Therefore, such a method is preferable. The pH of the final polymerization system before the system is neutralized is preferably 6 or less, more preferably 5 or less, even more preferably 4 or less and even more preferably 2 or less.

Chain Transfer Agent

The chain transfer agent has the ability of initiating a chain transfer reaction (growing polymer radicals react with other molecules, causing the transfer of a radical active point) and is a material added for the purpose of transferring chain units.

Examples of the chain transfer agent include a thiol type chain transfer agent and hydrocarbon halide type chain transfer agent, the thiol type chain transfer agent being preferable.

As the thiol type chain transfer agent, those having a —SH group are preferable, and those having a group represented by formula HS-R-Eg (wherein R represents a group derived from hydrocarbons having 1 to 4 carbon atoms, E represents —OH, —COOM, —COOR' or —SO$_3$M group, M represents a hydrogen atom, a monovalent metal, divalent metal, ammonium group or an organic amine group, R' represents an alkyl group having 1 to 10 carbon atoms and g denotes an integer from 1 or 2). Examples of the thiol type chain transfer agent include mercaptoethanol, thioglycerol, thioglycolic acid, 2-mercaptopropionic acid, 3-mercaptopropionic acid, thiomalic acid, octyl thioglycolate and octyl 3-mercaptopropionate. Mercaptopropionic acid and mercaptoethanol are preferable and mercaptopropionic acid is more preferable from the viewpoint of the chain transfer effect in the copolymerization reaction of the system including the polymerizable phosphate and the monomer (V). These compounds may be used either singly or in combinations of two or more.

Examples of the hydrocarbon halide type chain transfer agent include carbon tetrachloride and carbon tetrabromide.

Examples of other chain transfer agents may include an α-methylstyrene dimer, terpinolene, α-terpinene, γ-terpinene, dipenetene and 2-aminopropan-1-ol. These chain transfer agents may be used either singly or in combinations of two or more.

Initiator

In the production method of the present invention, it is preferable to use an initiator and the initiator is used in an amount of preferably 5 mol % or more, more preferably 7 to 50 mol % and even more preferably 10 to 30 mol % based on the total mols of the polymerizable phosphate and monomer (V).

As the aqueous type initiator, ammonium salts or alkali metal salts of persulfuric acid, hydrogen peroxide or water-soluble azo compounds such as 2,2'-azobis(2-amidinopropane)dihydrochloride and 2,2'-azobis(2-methylpropioneamide)dihydrate are used. Also, a promoter such as sodium hydrogen sulfite or amine compounds may be used in combination with the initiator.

Solvent

The production method of the present invention may be carried out by the solution polymerization method. Examples of the solvent used at this time include water and water-containing solvent type solvents containing water and methyl alcohol, ethyl alcohol, isopropyl alcohol acetone or methyl ethyl ketone. Water is preferable taking handling characteristics and reaction equipment into account. When particularly, an aqueous type solvent is used, a monomer solution containing the polymerizable phosphate is used at a pH of 7 or less, preferably 0.1 to 6 and more preferably 0.2 to 4 in the reaction to run a copolymerization reaction from the viewpoint of the uniformity of the monomer mixture solution (handling ability) and the reaction rate of the monomer and from the viewpoint of suppressing crosslinking by the hydrolysis of a pyro-form of a phosphoric acid compound.

An example of the production method of the present invention will be shown. A reactor is charged with a fixed amount of water, the atmosphere in the reactor is substituted with inert gas such as nitrogen and temperature in the reactor is raised. A solution obtained by mixing and dissolving the polymerizable phosphate, the monomer (V) and a chain transfer agent in water and a solution obtained by dissolving an initiator in water are prepared in advance. These solutions are added dropwise in the reactor over 0.5 to 5 hours. At this time, each monomer, the chain transfer agent and the initiator may be added dropwise separately. Also, a mixture solution containing the monomer is charged in the reactor and only the initiator may be added dropwise. In other words, the chain transfer agent, the initiator and other additives may be added in the form of an additive solution being different from the monomer solution. Alternatively they may be added to the monomer solution. From the viewpoint of a stable polymerization, on the other hand, they are preferably added in the form of an additive solution to the reaction system, separately from the monomer solution. In any case, each solution containing the polymerizable phosphate has preferably a pH of 7 or less. Also, the system is kept at a pH of 7 or less to run the copolymerization reaction by using an acid agent and preferably aged for a fixed time. In this case, the entire amount of the initiator may be added dropwise simultaneously with the monomer. Alternatively it may be added separately in divided amounts. It is preferable to add it in divided amounts from the viewpoint of reducing unreacted monomers. For example, it is preferable that ½ to ⅔ of the total weight of the initiator which is finally used be added simultaneously when the monomer is added and the remainder be added after the system is aged for 1 to 2 hours after the monomer is added. The reaction mixture is further neutralized by an alkali agent (for example, sodium hydroxide) after the aging is finished according to the need to obtain a phosphate polymer according to the present invention. The production method of the present invention is suitable for a method of producing a hydraulic composition dispersant containing the above phosphate polymer of the present invention.

The total amount of the polymerizable phosphate, monomer (V) and other copolymerizable monomers in the reaction system is preferably 5 to 80% by weight, more preferably 10 to 65% by weight and even more preferably 20 to 50% by weight.

Hydraulic Composition Dispersant

The phosphate polymer of the present invention may be used as the hydraulic composition dispersant for all inorganic type hydraulic powders, including various cements, exhibiting curability by a hydration reaction. A hydraulic composition dispersant containing the polymer of the present invention may have a powder form or a liquid form. When the hydraulic composition dispersant has a liquid form, it is preferably one using water as a solvent or dispersion medium (for example, an aqueous solution) from the viewpoint of workability and from the viewpoint of reducing the environmental load. The content of the polymer of the present invention in the dispersant of the present invention is preferably 10 to 100% by weight, more preferably 15 to 100% by weight and even more preferably 20 to 100% by weight on solid basis. Also, in the case of a liquid form, the solid concentration is preferably 5 to 40% by weight, more preferably 10 to 40% by weight and even more preferably 20 to 35% by weight from the viewpoint of productive easiness and workability. The dispersant in the present invention is used in a ratio by weight of 0.02 to 1 part by weight and 0.04 to 0.4 parts by weight as the solid content of the polymer based on 100 parts by weight of the hydraulic powder from the viewpoint of dispersing effect.

Examples of the cement include normal Portland cement, high early strength Portland cement, ultra high early strength Portland cement and eco-cement (for example, JIS R5214). As hydraulic powders other than cement, blast furnace slag, fly ash and silica fume may be contained and also, non-hydraulic lime stone micropowder may be compounded. Silica fume cement mixed with cement or blast furnace cement may be used.

The hydraulic composition dispersant in the present invention may contain other additives (materials). Examples of these additives may include AE agents such as a resin soap, saturated or unsaturated fatty acid, sodium hydroxystearate, lauryl sulfate, alkylbenzenesulfonic acid (salt), alkane sulfonate, polyoxyalkylene alkyl(phenyl)ether, polyoxyalkylene alkyl(phenyl)ether sulfate (salt), polyoxyalkylene alkyl (phenyl)ether phosphate (salt), protein materials, alkenylsuccinic acid and α-olefin sulfonate; retardants such as oxycarboxylic acid types such as gluconic acid, glucoheptonic acid, arabonic acid, malic acid and citric acid, sugar types such as dextrin, monosaccharides, oligo saccharides, polysaccharides and sugar alcohols; foaming agent; thickener; quarts sand; AE water-reducing agent; high early strength agents or promoters, for example, water-soluble calcium salts such as calcium chloride, calcium nitrite, calcium nitrate, calcium bromide and calcium iodide, chlorides such as iron chloride and magnesium chloride, sulfates, potassium hydroxide, sodium hydroxide, carbonates, thiosulfates, formic acid (salts) and alkanolamine; foaming agents; waterproof agents such as resin acids (salts), fatty acid esters, oil and fats, silicone, paraffin, asphalt and wax; blast furnace slag; fluidizing agents; antifoaming agents, for example, a dimethylpolysiloxane type, polyalkylene glycol fatty acid ester type, mineral oil type, oil and fat type, oxyalkylene type, alcohol type and amide type; foam proofing agents; fly ash; high-performance water-reducing agents, for example, polycarboxylic acid type including melaminesulfonic acid formalin condensate type, aminosulfonic acid type and polymaleic acid type; silica fume; rust preventives such as nitrites, phosphates and zinc oxide; water-soluble polymers, for example, natural product type such as a cellulose type such as methyl cellulose and hydroxyethyl cellulose, γ-1,3-glucan and xanthane gum, a synthetic type such as polyacrylic acid amide, polyethylene glycol, ethylene oxide adduct of oleyl alcohol or reaction products obtained by reacting the ethylene oxide adduct with vinylcyclohexene diepoxide; and emulsions of polymers such as alkyl(meth)acrylate.

Also, the hydraulic composition dispersant of the present invention is useful in all fields of various concretes for a self-leveling use, fire-proofing use, plaster use, gypsum slurry use, light-weight or heavy-weight concrete use, AE use, repair use, pre-packed use, tremie use, foundation improvement use, grout use and freezing weather use, besides the fields of ready-mixed concrete and concrete vibration products.

Hydraulic Composition

In the hydraulic composition which is the subject of the dispersant of the present invention, the ratio of water/hydraulic powder (the percentage ratio (wt %) of water to hydraulic powder in the hydraulic composition, which is designated by W/P hereinbelow) is preferably 65% or less, more preferably 10 to 60%, even more preferably 12 to 57%, even more preferably 15 to 55% and even more preferably 20 to 55%.

The hydraulic composition of the present invention is a paste, mortar or concrete containing water and a hydraulic powder (cement) and may contain an aggregate. Examples of the aggregate include fine aggregates and coarse aggregates. As the fine aggregates, pit sand, land sand, river sand and crushed sand are preferable, and as the coarse aggregates, pit gravel, land gravel, river gravel and crushed stone are preferable. Light weight aggregates may be used depending on use. Each term of these aggregates are quoted from "Comprehensive Bibliography of Concrete" (published on Jun. 10, 1998 by Gijutsu Shoin).

According to the present invention explained above, the present invention is a method of producing a polymerizable phosphate containing at least one selected from polymerizable phosphates represented by formula (II), (III) or (IV) by a batch reaction, including adding a compound represented by formula (I) into a mixture of a polymerizable phosphate reaction product containing at least one selected from polymerizable phosphates represented by formula (II), (III) or (IV), obtained by a pre-batch reaction, and phosphoric acid anhydride to react them.

Also, the present invention provides a hydraulic composition dispersant obtained by copolymerizing the polymerizable phosphate produced in the above method with a monomer represented by formula (V).

Also, a phosphate polymer is obtained in the presence of a chain transfer agent at a pH of 7 or less and the above hydraulic composition is provided in which the ratio Mw/Mn of the weight average molecular weight (Mw) to number average molecular weight of the obtained phosphate polymer is 1.0 to 2.6.

EXAMPLES

Figure 1:
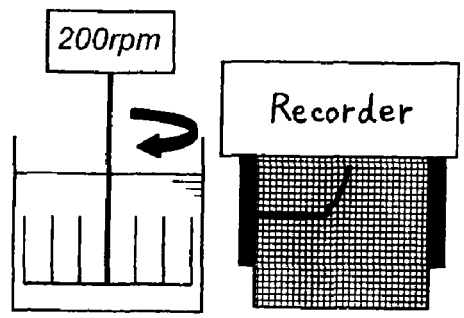
FIG. 1 is a schematic view of a torque tester and recorder used in the measurement of viscosity in Test Examples.

Examples are described below. However, the scope of the present invention is not limited by the following examples.

Comparative Example 1

A 2 L flask equipped with a stirrer, a temperature gage, a Dimroth condenser and a dropping funnel was charged with 742 g of hydroxyethylmethacrylate (hereinafter abbreviated as HEMA), 1.2 g of methoxyhydroquinone and 120 g of 75% phosphoric acid and these components were mixed while stirring. After that, the temperature of the mixture in the flask was raised to 80° C. while stirring and 336 g of phosphoric acid anhydride was poured into the flask from a powder funnel over 2 hours while using a water bath to remove the reaction heat produced by a phosphorylating reaction. Then, the mixture in the flask was kept at 80° C. by using warm water for 2 hours to carry out aging.

The composition of the reaction product was measured using a combination of $^{31}$P-NMR and gas chromatography, to determine that the effective content of the polymerizable phosphate was 49.3% by weight.
<Method of Measuring Effective Content>

It is generally known that phosphorous compounds can be analyzed by $^{31}$P-NMR. As to the composition of the reaction product, $^{31}$P-NMR and gas chromatography were used to make analysis in the following condition, thereby calculating the percentage composition. In the synthesis of the polymerizable phosphate, ethylene glycol dimethacrylate produced by the ester exchange reaction of HEMA exists as a material undetectable by $^{31}$P-NMR. This material was analyzed by gas chromatography in the following condition.

<Measuring Condition of $^{31}$P-NMR>
Measuring instrument: Mercury 400, 500 ΩHz
Solvent: Heavy methanol
Measuring temperature: Ambient temperature (20° C.)
Measuring method: Inverse-gated decoupling method
Observed data points: 10336
Pulse width: (5.833 μsec) 35° pulse
Range of measurement: 6459.9 Hz
Integrated number: 128
<Measuring Condition of Gas Chromatography>
Sample: Methylated using diazomethane
Column: Ultra ALLOY, 15 m×0.25 mm id×0.15 μm df
Carrier gas: He, split ratio 50:1
Column temperature: 40° C. (5 min)→10° C./min→300° C./15 min
Temperature of the injection port: 300° C.
Temperature of the detector: 300° C.

Comparative Example 2

A 3800 L SUS reactor which was equipped with a stirrer, a temperature gage, a condenser and a dropping feeder and which could be cooled by a jacket was charged while 1984 kg of HEMA, 3.2 kg of methoxyhydroquinone and 269 kg of 75% phosphoric acid and these components were mixed with stirring. Thereafter, cooling water kept at 7° C. was made to run through the jacket to cool the solution in the reactor while stirring continuously. Nitrogen and oxygen were blown into the reactor at a rate of 2.70 Nm$^3$-N$_2$/hr/m$^3$-reactor and at a rate of 0.05 Nm$^3$-O$_2$/hr/m$^3$-reactor respectively based on the volume of the reactor, and 950 kg of phosphoric acid anhydride was poured into the reactor over 6 hours while removing the reaction heat produced by the phosphorylating reaction such that the temperature in the reactor did not exceed 60° C. After that, the temperature of the mixture in the reactor was kept at 80° C. to carryout aging for 2 hours.

The composition of the reaction product obtained by the aging was measured in the same manner as in Comparative Example 1, to determine that the effective content of the polymerizable phosphate was 47.4% by weight.

Example 1

A 2 L flask was charged with 839 g of a polymerizable phosphate reaction product obtained in the same method as in Comparative Example 1. The effective content of the polymerizable phosphate in the reaction product was 48.4% by weight. 36 g of 75% phosphoric acid and 101 g of phosphoric acid anhydride were added to the above polymerizable phosphate while stirring.

After that, the temperature of the mixture in the flask was raised up to 80° C. by a water bath. After the temperature in the vessel reached 80° C., 223 g of HEMA was added dropwise by the dropping funnel over 3 hours while stirring while keeping the mixture at a fixed temperature. After that, the temperature of the mixture in the reactor was kept at 80° C. to carry out aging for 2 hours.

The composition of the reaction product obtained by the aging was measured in the same manner as in Comparative Example 1, to find that the effective content of the polymerizable phosphate was 52.7% by weight.

The polymerizable phosphate reaction product obtained by the aging contained the polymerizable phosphate reaction product charged in the first stage and therefore, the charged polymerizable phosphate was eliminated by calculation, to calculate the ratio of the effective content of the polymerizable phosphate to the total weight (B) of the charged 75% phosphoric acid, phosphoric acid anhydride and HEMA, with the result that the ratio was 62.7% by weight.

Example 2

A 2 L flask was charged with 875 g of a polymerizable phosphate reaction product obtained in the same method as in Comparative Example 1. The effective content of the polymerizable phosphate in the reaction product was 48.4% by weight. 101 g of phosphoric acid anhydride was added to the above polymerizable phosphate while stirring.

After that, the temperature of the mixture in the flask was raised up to 80° C. by a water bath. After the temperature in the vessel reached 80° C., 223 g of HEMA was added dropwise by the dropping funnel over 3 hours with while stirring while keeping the mixture at a fixed temperature. After that, the temperature of the mixture in the flask was kept at 80° C. to carry out aging for 2 hours.

The composition of the reaction product obtained by the aging was measured in the same manner as in Comparative Example 1, to find that the effective content of the polymerizable phosphate was 53.3% by weight.

The polymerizable phosphate reaction product obtained by the aging contained the polymerizable phosphate reaction product charged in the first stage and therefore, the charged polymerizable phosphate was eliminated by calculation, to calculate the ratio of the effective content of the polymerizable phosphate to the total weight (B) of the charged phosphoric acid anhydride and HEMA, with the result that the ratio was 66.5% by weight.

Example 3

A 2 L flask was charged with 594 g of a polymerizable phosphate reaction product obtained in the same method as in Comparative Example 1. The effective content of the polymerizable phosphate in the reaction product was 52.9% by weight. 52.0 g of 75% phosphoric acid and 67.3 g of phosphoric acid anhydride were added to the above polymerizable phosphate while stirring.

After that, the temperature of the mixture in the flask was raised up to 80° C. by a water bath. After the temperature in the vessel reached 80° C., 151.0 g of HEMA was added dropwise by the dropping funnel over 3 hours while stirring while keeping the mixture at a fixed temperature.

95.5 g of phosphoric acid anhydride was further added to this polymerizable phosphate reaction product while stirring.

After that, the temperature of the mixture in the flask was raised up to 80° C. by a water bath. After the temperature in the vessel reached 80° C., 206.7 g of HEMA was added dropwise by the dropping funnel over 3 hours while stirring while keeping the mixture at a fixed temperature.

After that, the temperature of the mixture in the flask was kept at 80° C. to carry out aging for 2 hours.

The composition of the reaction product obtained by the aging was measured in the same manner as in Comparative Example 1, to find that the effective content of the polymerizable phosphate was 61.5% by weight.

The polymerizable phosphate reaction product obtained by the aging contained the polymerizable phosphate reaction product charged in the first stage and therefore, the charged polymerizable phosphate was eliminated by calculation, to calculate the ratio of the effective content of the polymerizable phosphate to the total weight (B) of the charged phosphoric acid anhydride and HEMA, with the result that the ratio was 69.8% by weight.

Example 4

A 3800 L SUS reactor which was equipped with a stirrer, a temperature gage, a condenser and a dropping feeder and which could be cooled by a jacket was charged with 1972.6 kg of HEMA, 3.74 kg of methoxyhydroquinone and 314.6 kg of 75% phosphoric acid and these components were mixed while stirring. Thereafter, cooling water kept at 7° C. was made to run through the jacket to cool the solution in the reactor while stirring continuously. Nitrogen and oxygen were blown into the reactor at a rate of 2.70 Nm$^3$-N$_2$/hr/m$^3$-reactor and at a rate of 0.05 Nm$^3$-O$_2$/hr/m$^3$-reactor respectively based on the volume of the reactor, and 945.0 kg of phosphoric acid anhydride was poured into the reactor while removing the reaction heat produced by the phosphorylating reaction such that the temperature in the reactor did not exceed 60° C. After that, cooling water kept at 7° C. was made to run through the jacket to cool the solution in the reactor while stirring continuously, and 165.0 kg of phosphoric acid anhydride was poured into the reactor in such a manner that the temperature in the reactor did not exceed 80° C.

After that, warm water kept at 80° C. or more was made to run through the jacket to raise the temperature of the mixture in the reactor to 80° C. After the temperature in the reactor reached 80° C., 344 kg of HEMA was dripped from the dropping feeder over 2.3 hours while stirring while keeping the mixture at 80° C. Thereafter, the temperature of the mixture in the reactor was kept at 80° C. to carry out aging for 2 hours.

The composition of the reaction product obtained by the aging was measured in the same manner as in Comparative Example 1, to find that the effective content of the polymerizable phosphate was 52.9% by weight.

The polymerizable phosphate reaction product obtained by the aging contained the polymerizable phosphate reaction product charged in the first stage and therefore, the charged polymerizable phosphate was eliminated by calculation, to calculate the ratio of the effective content of the polymerizable phosphate to the total weight (B) of the charged phosphoric acid anhydride and HEMA, with the result that the ratio was 63.4% by weight.

Example 5

A 3800 L SUS reactor which was equipped with a stirrer, a temperature gage, a condenser and a dropping feeder and which could be cooled by a jacket was charged with 1691.3 kg of HEMA, 3.74 kg of methoxyhydroquinone and 314.6 kg of 75% phosphoric acid and these components were mixed while stirring. Thereafter, cooling water kept at 7° C. was made to run through the jacket to cool the solution in the reactor while stirring continuously. Nitrogen and oxygen were blown into the reactor at a rate of 2.70 Nm$^3$-N$_2$/hr/m$^3$-reactor and at a rate of 0.05 Nm$^3$-O$_2$/hr/m$^3$-reactor respectively based on the volume of the reactor, and 810.0 kg of phosphoric acid anhydride was poured into the reactor while removing the reaction heat produced by the phosphorylating reaction such that the temperature in the reactor did not exceed 60° C. After that, cooling water kept at 7° C. was made to run through the jacket to cool the solution in the reactor while stirring continuously, and 300.0 kg of phosphoric acid anhydride was poured into the reactor in such a manner that the temperature in the reactor did not exceed 80° C.

After that, warm water kept at 80° C. or more was made to run through the jacket to raise the temperature of the mixture in the reactor to 80° C. After the temperature in the reactor reached 80° C., 626.4 kg of HEMA was dripped from the dropping feeder over 2.3 hours while stirring while keeping the mixture at 80° C. Thereafter, the temperature of the mixture in the reactor was kept at 80° C. to carryout aging for 2 hours.

The composition of the reaction product obtained by the aging was measured in the same manner as in Comparative Example 1, to find that the effective content of the polymerizable phosphate was 52.9% by weight.

The polymerizable phosphate reaction product obtained by the aging contained the polymerizable phosphate reaction product charged in the first stage and therefore, the charged polymerizable phosphate was eliminated by calculation, to calculate the ratio of the effective content of the polymerizable phosphate to the total weight (B) of the charged phosphoric acid anhydride and HEMA, with the result that the ratio was 64.3% by weight.

The reaction conditions and results of Comparative Examples 1 and 2 and Examples 1 to 5 are shown collectively in Table 1.

TABLE 1

| | | Comparative example 1 | Example 1 | Example 2 | Example 3 | Example 4 (※3) | Comparative example 2 (※3) | Example 5 (※3) |
|---|---|---|---|---|---|---|---|---|
| Charge | | | | | | | | |
| Polymerizable phosphate reaction product (A) | (g) | — | 839 | 875 | 594 | 3236 | — | 2820 |
| (Effective content of the polymerizable phosphate) | (wt %) | | (48.4) | (48.4) | (52.9) | (48.4) | | (48.4) |
| HEMA (①) | (g) | 742 | 223 | 223 | 358 | 344 | 1984 | 626 |
| Methoxyhydroquinone (②) | (g) | 1.2 | — | — | — | — | 3.2 | — |
| 75% phosphoric acid (③) | (g) | 120 | 36 | 0 | 52 | 0 | 269 | 0 |
| Phosphoric acid anhydride (④) | (g) | 336 | 101 | 101 | 162 | 165 | 950 | 300 |
| Total of the added raw material (B = ① + ② + ③ + ④) | (g) | 1199 | 360 | 324 | 572 | 509 | 2934 | 926 |
| Total of the charge (T = A + B) | (g) | 1199 | 1199 | 1199 | 1166 | 3745 | 2934 | 3746 |
| (A/T) × 100 | (wt %) | 0 | 70 | 70 | 51 | 86 | 0 | 75 |
| Phosphorylating reaction | | | | | | | | |
| Reaction temperature | (° C.) | 80 | 80 | 80 | 80 | 80 | 60 | 80 |
| Reaction time | (hr) | 2.0 | 3.0 | 3.0 | 6.0 | 2.3 | 6.0 | 2.3 |
| Aging reaction | | | | | | | | |
| Aging temperature | (° C.) | 80 | 80 | 80 | 80 | 80 | 80 | 80 |
| Aging time | (hr) | 2.0 | 2.0 | 2.0 | 2.0 | 2.0 | 2.0 | 2.0 |
| Effective content of the polymerizable phosphate after aging (*1) | (wt %) | — | 52.7 | 53.3 | 61.5 | 52.9 | — | 52.9 |
| Effective content of the polymerizable phosphate after aging (*2) | (wt %) | 49.3 | 62.7 | 66.5 | 69.8 | 63.4 | 47.4 | 64.3 |

(*1): Effective content of the polymerizable phosphate based on the total charge (T)

(*2): Effective content of the polymerizable phosphate based on the total amount of the added raw material (B)

(※3): Each weight unit is kg (1) Production of a Dispersant

A 1000 ml container (four-neck flask) was charged with 397.2 g of water, the atmosphere in the container was substituted with nitrogen while stirring and the temperature of the system was raised to 80° C. in a nitrogen atmosphere. A solution obtained by mixing and dissolving 247.3 g of ω-methoxypolyethylene glycol monomethacrylate (addition molar number of ethylene oxides: 23), 64.7 g of the polymerizable phosphate composition obtained in Example 5 or Comparative Example 2 and 4.1 g of mercaptopropione in 159.5 g of ion exchange water and a solution obtained by dissolving 7.61 g of ammonium persulfate in 43.1 g of water were respectively added dropwise in the container over 1.5 hours. After the mixture was aged for one hour, a solution obtained by dissolving 1.67 g of ammonium persulfate in 9.5 g of water was added dropwise to the mixture over 30 minutes and the mixture was aged at 80° C. for 2 hours. After the aging was finished, the mixture was adjusted to pH 5.5 by adding an aqueous 30% sodium hydroxide solution to obtain a copolymer A of Example and a copolymer B of Comparative Example which were to be dispersants.

(2) Evaluation of Dispersibility and Viscosity

Using the obtained copolymer A, a test for the mortar formulation shown below was made to evaluate the dispersibility and viscosity of each formulation. The results are shown in Table 2.

(1) The materials used for the mortar formulation are shown in Table 2.

TABLE 2

| W/C | Unit amount (g/batch) | | |
|---|---|---|---|
| (%) | W | C | S |
| 40 | 160 | 400 | 700 |

C: Normal Portland cement (mixture of cements manufactured by Taiheiyo Cement Corporation and Sumitomo Osaka Cement Co., Ltd.)

W: Ion exchange water

S: Pit sand from Kimitsu in Chiba prefecture (fine aggregates that conform to the aggregate screening test of JIS A 1102 (all the aggregates passed through a screen having an opening of 10 mm and 85% or more of the aggregates passed through a screen having an opening of 5 mm))

(2) Preparation of Mortar

The ingredients shown in Table 1 were poured into a container (1 L stainless beaker) and a stirrer (EYELA Z-2310, manufactured by Tokyo RikaKikai CO., Ltd., Stirring bar: height 50 mm×6 bars/length 110 mm) was used to carry out kneading of the mixture at 200 rpm for 3 minutes, thereby preparing mortar. An antifoaming agent was added according to the need to adjust the mixture such that the amount of air to be entrained was 2% or less.

* Evaluation of Dispersibility

A corn having a top opening diameter of 70 mm, a bottom opening diameter of 100 mm and a height of 60 mm was used to evaluate the dispersibility of each mortar by the amount (effective content (% by weight) based on the cement) of the copolymer necessary to attain a mortar flow value of 220 mm. This mortar flow value (220 mm) is an average of the maximum value of the mortar flow value and a mortar flow value measured using a line segment having a length of ½ that of the line segment in a direction perpendicular to the direction in which the maximum mortar flow value is obtained. The smaller the amount of the copolymer is, the stronger the dispersibility is. In Table 3, the necessary amount of the copolymer A obtained in each example is shown here when the necessary amount of the copolymer B of Comparative Example is set to 100.

★ Evaluation of Viscosity

Figure 2:
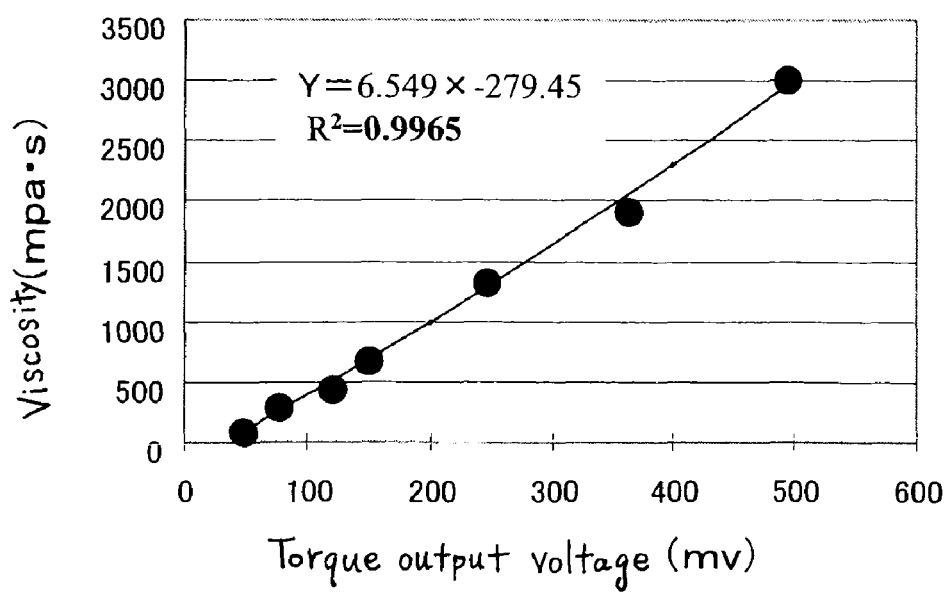
FIG. 2 is a view showing the relation of torque-viscosity of polyethylene glycol (Mw: 20,000) used for the calculation of viscosity in Test Examples.

A recorder was connected to a torque tester shown in FIG. 1 to measure the torque of the mortar. The viscosity of the mortar was calculated from the torque of the mortar based on the equation showing the relation between the torque and the viscosity of a polyethylene glycol (weight average molecular weight: 20,000) shown in FIG. 2. When the equation of the torque-viscosity characteristic of a polyethylene glycol is produced, the recorder recorded torque output voltage (mV) in the following condition: monitor output: 60 W and output signal: DC-0-5 V. The smaller the viscosity is, the stronger the effect of reducing viscosity is.

In Table 3, the viscosity of the copolymer A of Example is shown when the viscosity of the copolymer B obtained in Comparative Example.

TABLE 3

| Copolymer | Dispersibility (necessary amount to be added) % | Mortar viscosity % |
| --- | --- | --- |
| Copolymer A of Example | 89 | 77 |
| Copolymer B of Comparative Example | 100 | 100 |

The invention claimed is:

1. A method of producing a polymerizable phosphate comprising at least one compound selected from the group consisting of a polymerizable phosphate represented by the formula (II), (III), and (IV) by a batch reaction, the method comprising adding at least one compound represented by the formula (I) into a mixture of a polymerizable phosphate reaction product comprising the at least one compound selected from the group consisting of a polymerizable phosphate represented by the formula (II), (III) and (IV), wherein the polymerizable phosphate reaction product is obtained by a pre-batch reaction, and further by reacting with phosphoric acid anhydride, wherein the phosphoric acid anhydride is represented by the formula $P_2O_5$:

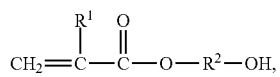

(I)

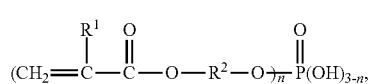

(II)

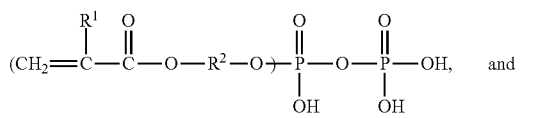

(III)

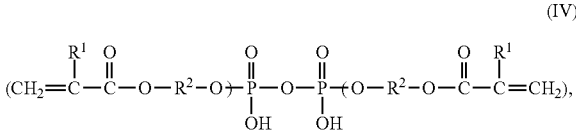

(IV)

wherein $R^1$ represents a hydrogen atom or a straight-chain or a branched alkyl group having from 1 to 4 carbon atoms, $R^2$ represents a straight-chain or a branched alkylene group having from 2 to 6 carbon atoms and n is an integer from 1 to 3.

2. The method according to claim 1, comprising repeating the batch reaction.

3. The method according to claim 1, wherein $R^1$ of the formulae (I) to (IV) is a methyl group.

4. The method according to claim 1, wherein $R^2$ of the formulae (I) to (IV) is an ethylene group.

5. The method according to claim 1, wherein the molar ratio of the phosphoric acid anhydride to the compound (I) is from 0.4 to 0.6.

6. The method according to claim 1, further comprising adding a polymerization inhibitor.

7. The method according to claim 6, wherein the amount of the polymerization inhibitor is from 10 ppm to 1.0 wt. % based on the total weight of the compound (I) and the phosphoric acid anhydride.

8. The method according to claim 1, wherein the temperature at which the compound (I) is added is 100° C. or less.

9. The method according to claim 1, wherein oxygen is blown into a reaction vessel.

10. The method according to claim 9, wherein the amount of the blown oxygen into the reaction vessel is 0.05 $Nm^3/hr/m^3$ or more based on the capacity of the reaction vessel.

11. The method according to claim 1, wherein the compound (I) is added over a period of time ranging from 0.5 to 10 hours.

12. The method according to claim 1, wherein an aging reaction is further carried out in succession to the addition the compound (I).

13. The method according to claim 12, wherein the aging time is from 0.5 to 10 hours.

14. The method according to claim 12, wherein the aging temperature is from 30 to 100° C.

15. The method according to claim 1, wherein at least one solvent selected from the group consisting of water and a water-containing solvent is added.

16. The method according to claim 1, wherein the water-containing solvent comprises water and at least one solvent selected from the group consisting of methyl alcohol, ethyl alcohol, isopropyl alcohol acetone, and methyl ethyl ketone.

* * * * *